United States Patent [19]

Kurz et al.

[11] Patent Number: 5,569,460
[45] Date of Patent: Oct. 29, 1996

[54] SKIN-COLORING PREPARATION

[75] Inventors: Thekla Kurz, Gross-Zimmern; Sieglinde Stossel, Reinheim; Andrea Spiller, Lemgo, all of Germany

[73] Assignee: Merck Patent Gesellschaft Mit Beschrankter Haftung, Darmstadt, Germany

[21] Appl. No.: 254,003

[22] Filed: Jun. 3, 1994

[30] Foreign Application Priority Data

Jun. 4, 1993 [DE] Germany .......................... 43 18 576.2

[51] Int. Cl.⁶ .......................... A61K 7/00; A61K 7/021; A61K 7/42
[52] U.S. Cl. .......................... 424/401; 424/59; 424/60; 424/63; 424/64
[58] Field of Search .............. 424/63, 64, 401, 424/59, 60

[56] References Cited

U.S. PATENT DOCUMENTS

| | | | |
|---|---|---|---|
| 3,506,758 | 4/1970 | Epstein et al. | 424/60 |
| 4,484,925 | 11/1984 | Roux | 8/94.26 |
| 4,900,541 | 2/1990 | Goviev | 424/47 |
| 5,232,688 | 8/1993 | Ziegler | 424/59 |

FOREIGN PATENT DOCUMENTS

| | | |
|---|---|---|
| 0077959 | 5/1983 | European Pat. Off. . |
| 456545 | 4/1991 | European Pat. Off. . |
| 500446 | 2/1992 | European Pat. Off. . |
| 2085208 | 12/1971 | France . |
| 0132243 | 10/1979 | Japan . |

OTHER PUBLICATIONS

Abstract of FR 2,085,208. Dec. 1971.
Abstract of EP 500,446. Feb. 1992.
Abstract of EP 456,545. Apr. 1991.

*Primary Examiner*—Gollamudi S. Kishore
*Attorney, Agent, or Firm*—Millen, White, Zelano, & Branigan, P.C.

[57] ABSTRACT

The invention relates to a skin-coloring preparation, containing a hydroxycarbonyl compound which has self-tanning properties, in a cosmetologically acceptable carrier, which preparation contains at least one colorant which adheres to the skin.

17 Claims, No Drawings

SKIN-COLORING PREPARATION

BACKGROUND OF THE INVENTION

The invention relates to a skin-coloring preparation, containing a hydroxycarbonyl compound which has self-tanning properties, in a cosmetologically acceptable carrier, which preparation contains at least one colorant which adheres to the skin.

It has been known for some time that compounds which have a keto group

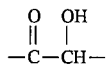

preferably hydroxymethylketones, in particular dihydroxyacetone, but also methyl glyoxal, have a self-tanning effect on human skin. This self-tanning effect is essentially based on a Maillard reaction between the keto group of these compounds and the amino acids of the skin.

Moreover, it is known that the hue obtained in this reaction can be further enhanced by adding certain adjuvants.

For example, EP 04 56 545 and EP 05 00 446 propose to employ indole derivatives, which were synthesized to resemble natural melamine, in such formulations. However, since their adhesion to the skin is relatively poor, they must be employed in relatively high concentrations.

According to FR 20 85 208, freckles can be produced artificially with formulations containing dihydroxyacetone and a water-soluble colorant However, the adhesion to the skin is poor, due to the solubility of these colorants in water.

Moreover, it has been proposed to prepare self-tanning formulations (for example U.S. Pat. No. 3,920,808 or U.S. Pat. No. 4,708,865) which contain, besides dihydroxyacetone, unsaturated ketones, for example lawsone or juglone. However, these produce an unnatural-looking, yellowish hue.

SUMMARY OF THE INVENTION

It has now been found that a coloration t of the skin which resembles a natural tan and lasts for a prolonged period can be achieved when the skin-coloring preparation contains, besides a hydroxycarbonyl compound, at least one colorant which adheres to the skin.

It was an object of the present invention to provide skin coloring preparations which cause a hue which resembles a natural tan and which lasts for a prolonged period. Surprisingly, it has now been found that such skin-coloring preparations are obtained when colorants which adhere to the skin are added to them.

The colorant which adheres to the skin is preferably an organic dye which adheres to the skin by physical attraction forces, but not by chemical bonding, like those of FR 2,085,208. The technical term for this behavior used by cosmeticians is 'substantivity'.

Preferably it is non-azo dye with at least one carbonyl and at least one phenolic group, the hydrogen or metal atom of which is not complexed intra-molecularly by said carboxy group. Furthermore it is preferably not a benzo- or naphtoquinone dye. Preferred are derivatives of 9-H-xanthen, in particular 9-phenyl substituted ones, as for example fluorescein derivatives of formula (I) below.

The following are preferred embodiments:

a) Skin-coloring, preparations in which the compound which has self-tanning properties is dihydroxyacetone or methyl glyoxal.

b) Skin-coloring preparations in which the colorant which adheres to the skin is a red solorant.

c) Skin-coloring preparations in which the colorant which adheres to the skin is an eosin derivative, preferably of the formula (I),

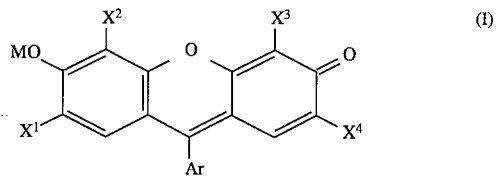

in which
$X^1$ to $X^4$ radicals, in each case independently of one another, are H, $NO_2$ or halogen, preferably Br or I, M is H or an alkali metal, preferably sodium, and Ar is a phenyl group which is substituted by a metal carboxylate group and which can optionally be substituted by 1 to 4 halogen atoms.

d) Skin-coloring preparations which contain 0.1 to 10, preferably 1 to 6, % by weight of a skin-coloring compound (i.e., the component with self-tanning properties) and 0.01 to 0.1, preferably approximately 0.05, % by weight of at least one colorant which adheres to the skin, in each case based on the total preparation.

e) Skin-coloring preparations, the ratio by weight between the colorant which adheres to the skin and the skin-coloring compound is greater than 0.01.

f) Skin-coloring preparations, in which the cosmetologically acceptable carrier is selected from the group comprising:
water;
a mixture of water and one or more organic components;
a mixture of fats and one or more organic solvents.

g) Skin-coloring preparations in which the organic components or solvents are selected from the group comprising:
the short-chain $C_{1-4}$-alcohols, long-chain $C_{10-18}$-monoalcohols, $C_{2-8}$-polyalcohols, alkylene glycols, glycol ethers, alkyl acetates, ethylene glycol $C_{1-3}$-monoalkyl ethers, and esters of the saturated $C_{14-16}$-fatty acids, in particular ethanol, cetyl alcohol, propylene glycol, ethylene glycol monoethyl ether and ethylene glycol monobutyl ether.

h) Skin-coloring preparations in which the fats are selected from the group comprising:
vegetable and animal oils, mineral oils, fatty acids, fatty alcohols, fatty acid esters and fatty acid triglycerides.

i) Skin-coloring preparations in which the pH is between 2 and 10, preferably between 3 and 6.

j) Skin-coloring preparations which contain at least one UV filter for the protection against UV-A and/or UV-B rays.

k) Skin-coloring preparations which contain surfactants, humectants, emollients, opacifying agents, dihydroxyindole derivatives, vitamins, perfumes, gelling agents, thickeners, pigments or preservatives.

The invention furthermore relates to a method for coloring the skin in a hue which resembles a natural tan, characterized in that a preparation according to one of claims 1 to 14 is applied to the skin, in particular a preparation is mixed with pigments or with other colorants which mask the hue of the colorant which adheres to the skin, preferably tartrazine (C.I. 19140), Solagen Brilliant Black (C.I. 28440), Brilliant Blue Acid Blue q (C.I. 42090) or Solvent Violet (C.I. 60725) to give a preferably brown make-up hue.

In a particularly preferred embodiment, the hue of the colorant which adheres to the skin is masked by natural, colored cosmetically active substances. These include, in particular, blue azulenes, such as guajazulene or chamuzulene, and yellow flavonoids, such as rutin or quercetin.

Preferred compounds which have self-tanning properties are those which have a keto group

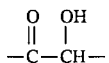

in particular dihydroxyacetone, methyl glyoxal, glycerol aldehyde, erythrulose, alloxan, 2,3-dihydroxysuccindialdehyde, 2,3-dimethoxysuccindialdehyde, 2-amino-3-hydroxysuccindialdehyde or 2-benzylamino-3-hydroxysuccindialdehyde.

Preferred colorants which adhere to the skin are eosin derivatives of the formula I, in particular eosin, erythrosin, bengal rose, phloxin, cyanosin, daphinin, eosin G, eosin 10B, Acid Red 51, in particular eosin G or erythrosin.

If the cosmetic preparation according to the invention is used as a composition for tanning the human epidermis, it is present in a range of forms which are conventionally used for this type. For example, it can be, in particular, in the form of oily or oily/alcoholic lotions, emulsions, such as a cream or a milk, in the form of oily/alcoholic, oily/aqueous or aqueous/alcoholic gels or in the form of solid sticks or else formulated as an aerosol.

It may contain cosmetic adjuvants which are conventionally used in this type of composition, such as, for example, thickeners, plasticizers, humectants, surfactants, preservatives, antifoams, perfumes, waxes, lanolin, propellants, colourants and/or pigments which impart color to the composition itself, UV filters for the protection against UV-A and/or UV-B rays and other ingredients customarily used in cosmetology.

An oil, wax or other fatty substance, a lower monoalcohol or a lower polyol or mixtures of these may be used as solubilizers. The particularly preferred monoalcohols or polyols include ethanol, i-propanol, propylene glycol, glycerol and sorbitol.

A preferred embodiment of the invention is an emulsion in the form of a cream or milk and includes, in addition to the compound of the formula I, fatty alcohols, fatty acid esters, in particular fatty acid triglycerides, fatty acids, lanolin, natural or synthetic oils or waxes and emulsifiers in the presence of water.

Other preferred embodiments are oily lotions based on natural or synthetic oils and waxes, lanolin; fatty acid esters, in particular fatty acid triglycerides, or oily/alcoholic lotions based on a lower alcohol, such as ethanol, or a glycol, such as propylene glycol and/or polyol, such as glycerol, and oils, waxes and fatty acid esters, such as fatty acid triglycerides.

The cosmetic composition according to the invention can also be in the form of an alcoholic gel which includes one or more lower alcohols or lower polyols, such as ethanol, propylene glycol or glycerol, and a thickener, such as silica. The oily/alcoholic gels additionally contain a natural or synthetic oil or wax.

The solid sticks are composed of natural or synthetic waxes and oils, fatty alcohols, fatty acid esters, lanolin and other fatty substances.

The invention also relates to cosmetic suncare products which may include at least one α-hydroxycarbonyl compound having self-tanning properties, at least one colorant which adheres to the skin and UVB and/or UVA filters.

Examples of suitable UV filters are cinnamic acid derivatives, benzylidene camphor and its derivatives, p-aminobenzoic acid and its derivatives salicylic acid derivatives, benzophenone derivatives and dibenzoylmethane derivatives. As a rule, the preparations contain 0.2 to 10% by weight of these UV filters, base on compounds having self-tanning properties.

If a preparation is formulated as an aerosol, the conventional propellants, such as alkanes, fluoroalkanes chlorofluoroalkanes are generally used.

If appropriate, the preparation according to the invention may contain thickeners:

The thickeners or gelling agents known to the person skilled in the art can be used for thickening, examples being guar gum, heterobiopolysaccharides, xanthan gum, scleroglucans, cellulose derivatives, such as, for example, methylcellulose, hydroxyethylcellulose, hydroxymethylpropylcellulose, alkali metal salts of carboxymethylcellulose, and polyacrylic acids.

Since the colorant which adheres to the skin shows an intrinsic color not only when the self-tan develops but already in the formulation and on the skin, it is particularly advantageous to mask the hue of the colorant which adheres to the skin by adding pigments or other colorant s which impart a brown make-up tone together with the colorant which adheres to the skin.

The invention furthermore relates to cosmetic preparations which contain a) an α-hydroxycarbonyl compound which has self-tanning properties in an amount of preferably 0.1 to 10% by weight, based on the preparation, b) a colorant which adheres to the skin in an amount of preferably 0.01 to 0.1% by weight, based on the composition, c) a color-imparting pigment, in particular an effect pigment, e.g. a nacreous pigment, based on a metal-oxide-coated, platelet-shaped substrate, in an amount of preferably 1 to 15% by weight, based on the composition, or d) some other colorant, in particular a colorant which masks the hue of the colorant which adheres to the skin, preferably in an amount of 0.01 to 0.1% by weight, based on the composition, and e) if appropriate, titanium dioxide, preferably in an amount of 1 to 10% by weight, based on the composition.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. P4318576.2 filed Jun. 4, 1993, are hereby incorporated by reference.

EXAMPLES

Example 1

Tinted self-tanning milk

|   |   |   | % |
|---|---|---|---|
| A | Arlatone 983 S | (2) | 1.50 |
|   | Arlatone 985 | (2) | 2.50 |
|   | Brij 76 | (2) | 1.50 |
|   | Liquid paraffin (Article No. 7162) | (1) | 5.00 |
|   | Miglyol 812 | (3) | 5.00 |
| B | Karion F liquid (Article No. 2993) | (1) | 2.50 |
|   | 1,2-propanediol (Article No. 7478) | (1) | 2.50 |
|   | 1% eosin G solution (Article No. 15935) | (1) | 5.00 |
|   | Preservative | (1) | q.s. |
|   | Demineralized water |   | to 100.000 |
| C | Dihydroxyacetone (Article No. 10150) | (1) | 5.00 |
|   | Demineralized water | (1) | 5.00 |
| D | Pigment Transparent Yellow Ochre (Article No. 17381) | (1) | 7.00 |
|   | Pigment Transparent Black (Article No. 17161) | (1) | 1.00 |
|   | Titanium dioxide 1171 | (4) | 6.00 |

Preparation:

Heat phase A at 75° C. and phase B at 80° C. Slowly stir phase B into phase A. Homogenize. Cool with stirring, add phase C when mixture has reached 40° C. Finally, slowly stir in the pigments.

Notes:

The samples contain 0.05% of propyl 4-hydroxybenzoate (Merck Article No. 7427) and 0.15% of methyl 4-hydroxybenzoate (Merck Article No. 6757)

as preservatives.

Suppliers:
1. E. Merck, Darmstadt
2. ICI, Essen
3. Hüls Troisdorf AG, Witten
4. Kronos Titan GmbH, Leverkusen Use Example 1:

The preparation prepared in Example 1 is applied to various subjects.

The resulting hues are evaluated after 21.5 hours (Table 1) and 45 hours (Table 2) using the so-called Lab method (for example in accordance with Ullmann's Encyclopedia of Industrial Chemistry, Vol. A 20, p. 262–263, 1992, Verlag Chemie)

L=Lightness a=Red content b=Yellow content

C=Chroma

H=Hue angle and compared with the corresponding hues without skin-coloring preparation or with skin-coloring preparation but without colorant which adheres to the skin.

Using the preparation according to the invention, a considerably higher red content is achieved even after prolonged exposure and repeated washing, while the chroma (C) is approximately the same.

TABLE 1

| Skin Subject | Blank |  |  |  |  |
|---|---|---|---|---|---|
|  | L | a | b | C | H |
| Values 21.5 hours after application |  |  |  |  |  |
| 1 | 61.616 | 7.453 | 13.715 | 15.6091 | 61.4771 |
| 2 | 60.909 | 6.336 | 12.769 | 14.254 | 63.6102 |
| 3 | 60.891 | 5.65 | 12.39 | 13.6177 | 65.4868 |
| 4 | 52.605 | 8.12 | 17.264 | 19.0783 | 64.8117 |
| 5 | 70.802 | 4.384 | 18.105 | 18.6284 | 76.3887 |
| 6 |  |  |  |  |  |
| 7 | 65.032 | 4.844 | 11.888 | 12.8369 | 67.8308 |
| 8 | 63.583 | 6.633 | 14.003 | 15.4949 | 64.6539 |
| *9 | 58.032 | 9.233 | 17.99 | 20.221 | 62.8332 |
| 10 | 63.251 | 5.678 | 13.373 | 14.5286 | 66.9963 |
| 11 | 66.761 | 7.523 | 15.351 | 17.0952 | 63.8931 |
| 12 | 68.987 | 3.288 | 8.341 | 8.9656 | 68.486 |
| After application of a preparation containing 5.4% of DHA |  |  |  |  |  |
| 1 | 57.91 | 9.8 | 19.017 | 21.3935 | 62.7351 |
| 2 | 55.621 | 9.475 | 17.817 | 20.1795 | 61.9943 |
| 3 | 59.368 | 8.913 | 16.726 | 18.9526 | 61.9493 |
| 4 | 53.898 | 11.147 | 19.593 | 22.5425 | 60.3635 |
| 5 | 62.783 | 9.07 | 20.896 | 22.7792 | 66.5364 |
| 6 | 60.458 | 8.744 | 16.567 | 18.7327 | 62.1761 |
| 7 | 65.635 | 6.313 | 14.599 | 15.9051 | 66.615 |
| 8 | 60.517 | 9.366 | 17.503 | 19.8514 | 61.85 |
| 9 | 52.019 | 11.077 | 23.282 | 25.7824 | 64.5564 |
| 10 | 58.205 | 9.643 | 18.881 | 21.201 | 62.9458 |
| 11 | 52.914 | 11.443 | 20.881 | 23.8111 | 61.2762 |
| 12 | 63.747 | 8.059 | 17.46 | 19.2298 | 65.2241 |
| After application of a preparation containing 4.0% of DHA + 0.05% of eosin |  |  |  |  |  |
| 1 | 60.415 | 10.547 | 16.661 | 19.56 | 58.4074 |
| 2 | 65.729 | 10.578 | 16.019 | 19.1966 | 56.5625 |
| 3 | 61.63 | 9.389 | 15.792 | 18.3724 | 59.2686 |
| 4 | 53.327 | 12.512 | 19.143 | 22.8694 | 56.8318 |
| 5 | 60.481 | 7.399 | 16.752 | 18.3135 | 66.1703 |
| 6 | 58.744 | 8.195 | 14.804 | 16.9205 | 61.0328 |
| 7 | 64.915 | 7.607 | 14.611 | 16.4726 | 62.4972 |
| 8 | 56.53 | 9.517 | 17.313 | 19.757 | 61.2019 |
| 9 | 52.775 | 10.482 | 21.949 | 24.3238 | 64.473 |
| 10 | 57.883 | 10.267 | 15.987 | 18.9998 | 57.2921 |
| 11 | 57.932 | 13.085 | 17.936 | 22.2018 | 53.8894 |
| 12 | 65.478 | 6.853 | 13.667 | 15.2813 | 63.3696 |
| Control value: Subject 13 after summer holidays |  |  |  |  |  |
| Arm, dark | 49.5908 | 10.662 | 18.294 | 21.1745 | 59.7654 |
| Arm, pale | 53.241 | 10.089 | 18.339 | 20.9308 | 61.184 |

*Subject 9 had only been back from holidays for 2 weeks

TABLE 2

| Values 45 hours after application |  |  |
|---|---|---|
|  | C | H |
| DHA subject |  |  |
| 1 | 22.1871 | 64.1365 |
| 2 | 18.4367 | 65.4451 |
| 3 | 18.5933 | 64.3664 |
| 4 | 23.6082 | 60.5514 |
| 5 | 22.7578 | 67.9486 |
| 6 | 18.6948 | 62.0513 |
| 7 | 15.876 | 72.3164 |
| 8 | 18.4847 | 61.6671 |
| 9 | 23.6388 | 64.5476 |
| 10 | 20.6111 | 63.216 |
| 11 | 19.0048 | 62.8249 |

TABLE 2-continued

| | Values 45 hours after application | |
|---|---|---|
| | C | H |
| 12 DHA + eosin subject | 18.04 | 66.0599 |
| 1 | 20.8885 | 62.8327 |
| 2 | 18.8088 | 61.9299 |
| 3 | 19.831 | 62.4987 |
| 4 | 21.5169 | 59.5625 |
| 5 | 21.1785 | 67.964 |
| 6 | 15.9307 | 63.283 |
| 7 | 15.694 | 68.1098 |
| 8 | 19.0126 | 60.972 |
| 9 | 22.6928 | 63.9565 |
| 10 | 17.7356 | 57.3972 |
| 11 | 19.6395 | 62.4783 |
| 12 | 14.8434 | 68.4706 |

Use Example 2:

A composition prepared as in Example 1 is applied to a subject and compared in each case with a composition which contains lawsone or no colorant instead of eosin G:

The resulting hues are evaluated after 21.5 hours (Table 3).

The composition according to the invention results in a smaller hue angle H, i.e. a reddish brown, than the lawsone-containing composition, which causes a yellowish brown hue:

TABLE 3

| Formulation | 5% DHA | 5% of DHA + lawsone | 5% of DHA + eosin G |
|---|---|---|---|
| H | 65.2241 | 78.3972 | 59.2559 |

Examples 2–7: Tinted self-tan creams
Preservative:

| | | | % |
|---|---|---|---|
| A | Emulsifier E 2155 | (2) | 8.000 |
| | Liquid paraffin (Article No. 7162) | (1) | 12.000 |
| | Pourable paraffin (Article No. 7158) | (1) | 2.000 |
| | Miglyol 812 | (3) | 3.000 |
| | Isopropyl myristate | (4) | 2.000 |
| B | 1,2-propanediol (Article No. 7478) | (1) | 4.000 |
| | Karion F liquid (Article No. 2993) | (1) | 2.000 |
| | Colorant mix (as in Table 4) | | 5.000 |
| | Preservative | | q.s. |
| | Demineralized water | | to 100.000 |
| C | Dihydroxyacetone (Article No. 10150) | (1) | 5.000 |
| | Demineralized water | | 11.800 |

0.05% of propyl 4-hydroxybenzoate (Merck Article No. 7427)

0.15% of methyl 4-hydroxybenzoate (Merck Article No. 6757)

Suppliers:
1. E. Merck, Darmstadt
2. Th. Goldschmidt, Essen
3. Hüls Troisdorf AG, Witten
4. Henkel, Düsseldorf Preparation:

Heat phase A at 75° C. and phase B at 80° C. Slowly stir phase B into phase A. Homogenize. Stir, add phase C when the mixture has reached 40° C.

TABLE 4

| Colourant mixers | | | |
|---|---|---|---|
| Example | Eosin G | Tartrazine | Solagen Brilliant Black |
| 2 | 3% | 6.2% (11.4%) | 1.24% (2.28%) |
| 3 | 5% | 6.2% (11.4%) | 1.24% (2.28%) |
| 4 | 7% | 6.2% (11.4%) | 1.24% (2.28%) |
| Example | Erythosin I | Tartrazine | Solagen Brilliant Black |
| 5 | 2% | 11.4% | 2% |
| 6 | 4% | 11.4% | 2% |
| 7 | 6% | 11.4% | 2% |

Note

The solutions have a strength of 1% and are added to the aqueous phase.

Eosin G (C.I. 45380)

Solagen Brilliant Black (C.I. 28440)

Tartrazine (C.I. 19140)

Erythrosin I (C.I. 45439)

All colorants are listed in the Blue Liste.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a skin-coloring composition comprising a compound having self-tanning properties which is dihydroxyacetone or methylglyoxal, and a cosmetologically acceptable carrier, the improvement wherein the composition contains at least one colorant which adheres to the skin, which is an eosin compound with at least one carbonyl group and at least one phenolic group with a hydrogen or metal atom which is not complexed intramolecularly by the carbonyl group.

2. A skin-coloring composition according to claim 1, wherein the colorant which adheres to the skin is eosin G or erythrosin I.

3. A skin-coloring composition according to claim containing 0.1 to 10% by weight of the compound with self-tanning properties and 0.01 to 0.1% by weight of at least one colorant which adheres to the skin, in each case based on the total composition.

4. A skin-coloring composition according to claim 1, wherein the ratio by weight between the colorant which adheres to the skin and the compound with self-tanning properties is greater than 0.01.

5. A skin-coloring composition according to claim 1, wherein the cosmetologically acceptable carrier is
   (a) water;
   (b) a mixture of water and at least one short chain $C_{1-4}$-alcohol, long-chain $C_{10-18}$-mono-alcohol, $C_{2-8}$-polyalcohol, glycol ether, alkyl acetate, or ester of a saturated $C_{14-16}$-fatty acid; or
   (c) a mixture of fats and at least one organic solvent.

6. A skin-coloring composition according to claim 5, wherein the organic solvent is ethanol, cetyl alcohol, propylene glycol, ethylene glycol monoethyl ether or ethylene glycol monobutyl ether.

7. A skin-coloring composition according to claim 5, wherein the fat is a vegetable or animal oil, a mineral oil, a fatty acid, a fatty acid ester or a fatty acid triglyceride.

8. A skin-coloring composition according to claim 1 having a pH of 2 to 10.

9. A skin-coloring composition according to claim 1 containing at least one compound which acts as a filter for UV-A and/or UV-B rays.

10. A skin-coloring composition according to claim 1 containing a surfactant, humectant, emollient, opacifying agent, dihydroxyindole compound, vitamin, perfume, gelling agent, thickener, additional pigment, or a preservative.

11. A skin-coloring composition according to claim 10, wherein the additional pigment is a pearlescent pigment.

12. A method of coloring human skin in a hue which resembles a natural tan, comprising applying to the skin a preparation according to claim 1.

13. A skin-coloring composition according to claim 1, wherein the eosin compound has the formula:

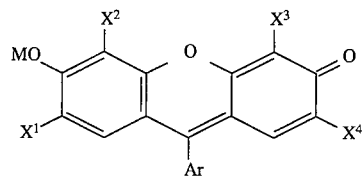

wherein $X^1$ to $X^4$ are each independently H, $NO_2$ or halogen,

M is H or an alkali metal, and

Ar is a phenyl ring substituted with a metal carboxylate group, and optionally substituted by 1–4 halogen atoms.

14. A skin-coloring composition according to claim 13, wherein $X^1$ to $X^4$ are each independently Br or I, and M is Na.

15. A skin-coloring composition according to claim 10, wherein the colorant which masks the hue of the colorant which adheres to the skin is tartrazine (C.I. 19140), Solagen Brilliant Black (C.I. 28440), Brilliant Blue Acid Blue q (C.I. 42090), Solvent Violet (C.I. 60725), a blue azulene or a yellow flavenoid.

16. A compound according to claim 5, wherein the glycol ether is an ethylene glycol-$C_{1-3}$-monoalkyl ether.

17. A method of coloring human skin in a hue which resembles a natural tan, comprising applying to the skin e preparation according to claim 13.

* * * * *